United States Patent [19]

Poterack

[11] Patent Number: 5,386,821
[45] Date of Patent: Feb. 7, 1995

[54] BITE BLOCK FOR ORAL PASSAGEWAY

[76] Inventor: Karl A. Poterack, 4422 Shavano Cross, San Antonio, Tex. 78230

[21] Appl. No.: 73,537

[22] Filed: Jun. 8, 1993

[51] Int. Cl.$^6$ .................. A61M 16/00; A62B 9/06; A61C 5/14
[52] U.S. Cl. ................ 128/200.26; 128/207.14; 128/DIG. 26; 128/859; 128/861
[58] Field of Search ............ 128/201.11, 200.26, 128/207.14, 859, 861, 912, DIG. 26

[56] References Cited

U.S. PATENT DOCUMENTS

| | | |
|---|---|---|
| 316,636 | 4/1885 | Miles . |
| 2,669,988 | 2/1954 | Carpenter . |
| 2,693,182 | 11/1954 | Phillips . |
| 2,705,959 | 4/1955 | Elmore . |
| 2,820,457 | 1/1958 | Phillips . |
| 2,857,911 | 10/1958 | Bennett . |
| 2,882,893 | 4/1959 | Godfroy . |
| 2,908,269 | 10/1959 | Cheng . |
| 3,090,122 | 5/1963 | Erickson . |
| 3,106,916 | 10/1963 | Matthes . |
| 3,126,002 | 3/1964 | Owens . |
| 3,139,088 | 6/1964 | Galleher, Jr. . |
| 3,167,072 | 1/1965 | Stone et al. . |
| 3,228,107 | 1/1966 | Zandberg . |
| 3,306,298 | 2/1967 | Raimo . |
| 3,496,936 | 2/1970 | Gores . |
| 3,518,988 | 7/1970 | Gores ................ 128/861 |
| 3,542,321 | 11/1970 | Kahabla . |
| 3,568,680 | 3/1971 | Raimo . |
| 3,576,187 | 4/1971 | Odders . |
| 3,768,465 | 10/1973 | Helmer . |
| 3,774,616 | 11/1973 | White et al. . |
| 3,924,636 | 12/1975 | Addison . |
| 3,930,507 | 1/1976 | Berman . |
| 3,976,080 | 8/1976 | Bornhorst et al. ......... 128/DIG. 26 |
| 3,977,407 | 8/1976 | Coleman et al. . |
| 4,030,493 | 6/1977 | Walters et al. . |
| 4,031,888 | 6/1977 | Walters .............. 128/859 |
| 4,090,518 | 5/1978 | Elam . |
| 4,112,936 | 9/1978 | Blachly . |
| 4,166,467 | 9/1979 | Abramson . |
| 4,167,946 | 9/1979 | Sandstrom . |
| 4,198,970 | 4/1980 | Luomanen . |
| 4,223,671 | 9/1980 | Muto . |
| 4,256,099 | 3/1981 | Dryden . |
| 4,270,529 | 6/1981 | Muto . |
| 4,326,515 | 4/1982 | Shaffer et al. . |
| 4,329,984 | 5/1982 | Kervin . |
| 4,331,143 | 5/1982 | Foster . |
| 4,344,428 | 8/1982 | Sherman . |
| 4,351,331 | 9/1982 | Gereg . |
| 4,356,821 | 11/1982 | Rind . |
| 4,425,911 | 1/1984 | Luomanen et al. . |
| 4,495,945 | 1/1985 | Liegner . |
| 4,519,386 | 5/1985 | Sullivan .............. 128/859 |
| 4,527,559 | 7/1985 | Roxburg et al. . |
| 4,640,273 | 2/1987 | Greene et al. . |
| 4,744,358 | 5/1988 | McGinnis . |
| 4,832,019 | 5/1989 | Weinstein et al. . |
| 4,896,667 | 1/1990 | Magnuson et al. . |
| 4,901,737 | 2/1990 | Toone . |
| 5,009,227 | 4/1991 | Nieuwstad . |
| 5,031,611 | 7/1991 | Moles ................ 128/201.11 |
| 5,062,422 | 11/1991 | Kinkade ............. 128/201.11 |
| 5,152,301 | 11/1992 | Kittelsen et al. ........ 128/861 |
| 5,203,324 | 4/1993 | Kinkade ............. 128/201.11 |
| 5,339,832 | 8/1994 | Kittelsen et al. ........ 128/861 |

FOREIGN PATENT DOCUMENTS 92803  5/1962  Denmark ............ 128/200.26

Primary Examiner—Kimberly L. Asher
Attorney, Agent, or Firm—Gunn, Lee & Miller

[57] ABSTRACT

The device of the present invention is a bite block for use with endotracheally intubated patients. The bite block is generally U-shaped and made of a hard but pliable material. The termini of each of the legs of the "U" are wedge shaped, being thinner at the terminus of each leg. A curved rib connects the two legs. The combination of the wedge-shaped legs and the curved rib allow the interjaw compressive forces to be borne by the molars rather than the incisors or front teeth.

9 Claims, 4 Drawing Sheets

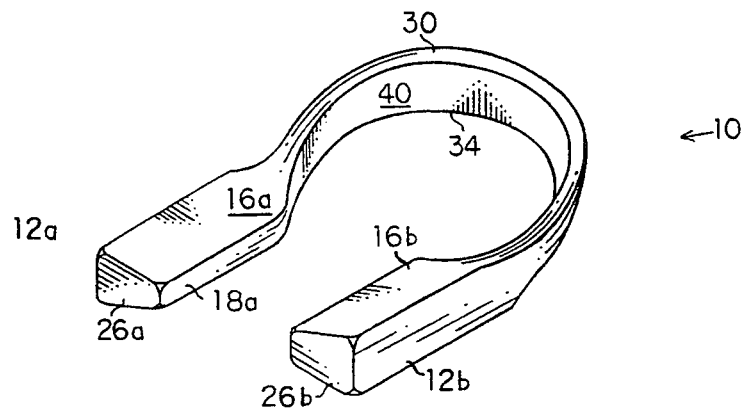
FIG. 5
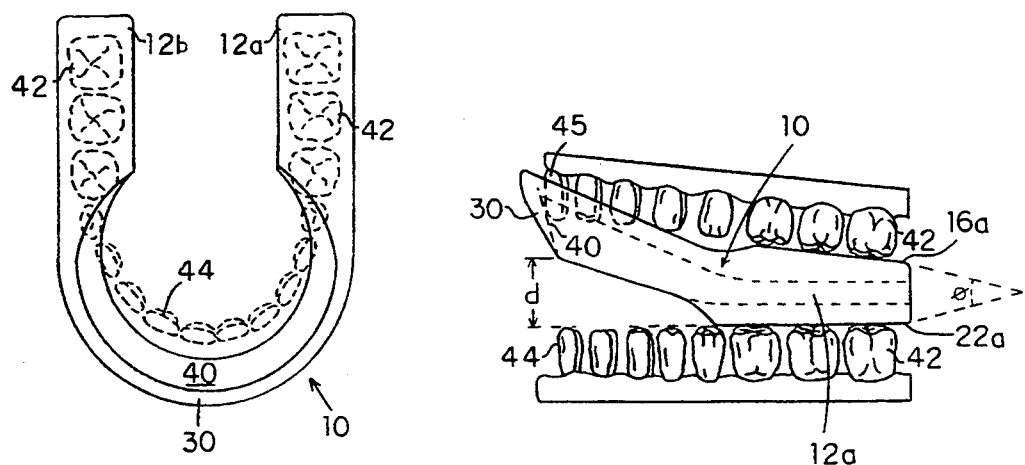
FIG. 6   FIG. 8

BITE BLOCK FOR ORAL PASSAGEWAY

FIELD OF THE INVENTION

The invention relates to bite blocks, more specifically, bite blocks for intubated patients in which the compressive force resulting from the closure of the jaws is borne by the molars.

BACKGROUND OF THE INVENTION

A device, commonly called a bite block, is used to prevent patients emerging from general anesthesia who are endotracheally intubated, as well as patients who are intubated for respiratory failure, from struggling and biting down on the endotracheal tubes and occluding the airway. The endotracheal tubes are constructed of pliable plastic and can be easily crushed. If this occurs, the patients are exposed to risks of hypoventilation, pulmonary edema, hypoxia, asphyxia, and even death. In addition, patients requiring fiber-optic examination of the respiratory and gastrointestinal tract via the oral route are sometimes noncooperative and can bite down on the endoscopes, causing damage to the scopes and/or their teeth. Further, patients undergoing electro-convulsive therapy or electrical cardioversion often clinch their jaws and damage their teeth and other intra-oral structures. The bite block is, therefore, a simple device to prevent jaw closure by providing a physical obstruction between the teeth set in the upper and lower jaws.

A number of U.S. patents are directed to various bite block designs. These include U.S. Pat. No. 4,425,911 which discloses a bite block for patients intubated with endotracheal tubes. The '911 bite block includes a body which has apertures communicating with channels for accommodating intubation of the endotracheal tube and suction catheter.

U.S. Pat. No. 4,495,945 discloses a bite block which is employed in conjunction with endoscopy, bronchoscopy, endotracheal intubation and the like. The bite block includes upper and lower surfaces for contacting teeth, including incisor and front teeth, and carrying the pressure of the same compressively.

However, both patents reflect a major drawback of the prior art. That is, they disclose bite blocks in which non-molar teeth bear some of the compressive forces between the jaws. Prior art bite blocks provide for intra-oral structures other than the molars (such as tongue, palate, incisors, front teeth, etc.) to bear some of the substantial pressures brought to bear in affixing and maintaining a bite block in the patient's mouth. This increases the risk of pressure necrosis to these sensitive structures. For example, the geometry of the incisors is such that they can bear materially less compressive forces without fracture than can the molars. It is the structure and geometry of the molars that make them the strongest oral structures for bearing compressive forces.

Much of the prior art includes devices which are unnecessarily cluttered in design and prevent and/or impede the easy passage of an endotracheal tube after insertion of the bite block. The bite blocks of the prior art are designed to combine the features of a bite block and an oral airway—to elevate the tongue and jaw from the posterior pharynx and provide an airway in an unconscious or semiconscious patient. That is, the oral airways of prior art are designed to include bite blocks. Unfortunately, they carry the disadvantage that the compressive forces of the jaws are, in material part, borne by the central incisors, which, due to the narrow depth and relative height, are prone to breakage. In addition, compressive force borne by the central incisors results in unfavorable loading conditions on the temporal mandibular joint. Additionally, pressure of the intra-oral terminus of the airway on the tongue and palate can cause patient discomfort, stimulation of the gag reflex with consequent regurgitation, pressure necrosis of the tongue and palate, and cranial nerve injuries.

Thus, it is the several objects and advantages of the novel bite block set forth herein to carry the compressive forces between the molars and provide free access to the oropharynx for suctioning, fiberoptic examination of the gastrointestinal tract and the like, as well as for providing for a bite block that can be easily placed in the patient's mouth before or after direct laryngoscopy.

It is a further object of the present invention to provide a bite block for intubated patients in the operating room or the intensive care unit, which patients require fiberoptic examination of the respiratory or gastrointestinal tracts, electroconvulsive therapy, electrical cardioversion or similar procedures.

It is a further object of the present invention to provide a bite block that lends itself to easy fixation in a patient's mouth and facilitates fixation of an endotracheal tube in the patient's mouth.

SUMMARY OF THE INVENTION

These and other objects are provided for in a bite block constructed of a soft, pliable material which has a U-shaped body having peripheral surfaces preferably curved to conform with the curve of Spree, the anatomical term given to the natural curvature of the dental ridge, having two wedge-shaped members at the terminus thereof. The wedge-shaped members are connected by a substantially-curved rib and have a different thickness along an inner edge thereof than along the outer edge thereof. The wedge members are further tapered to be thinner at the terminus thereof.

BRIEF DESCRIPTION OF THE FIGURES

FIG. 5 is a rear, top, right side perspective view of the bite block of the present invention.

FIG. 6 is a top elevational view of the bite block of the present invention as inserted into the mouth of a patient illustrating the relationship between the position of the bite block and the patient's lower teeth.

FIG. 8 is a side elevation view of the bite block of applicant's present invention inserted into the mouth of a patient showing the relationship between the teeth of the patient and the bite block.

DETAILED DESCRIPTION OF THE PREFERRED EMBODIMENT

Figure 1:
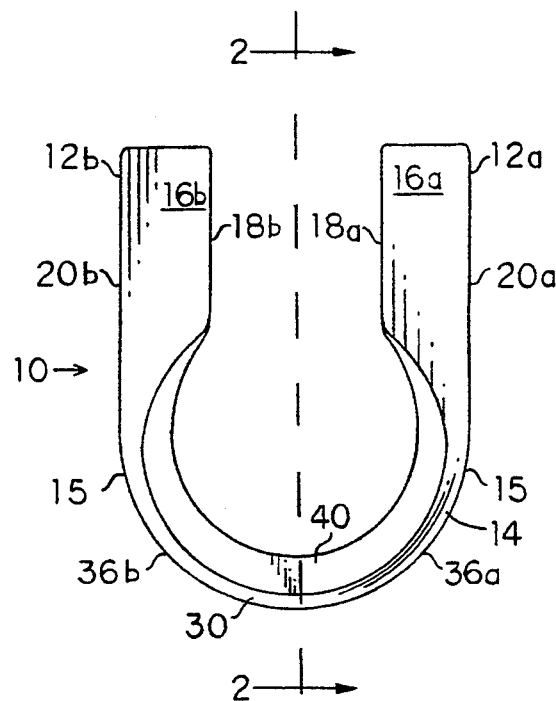
FIG. 1 is a top elevational view of the bite block of the present invention.
Figure 2:
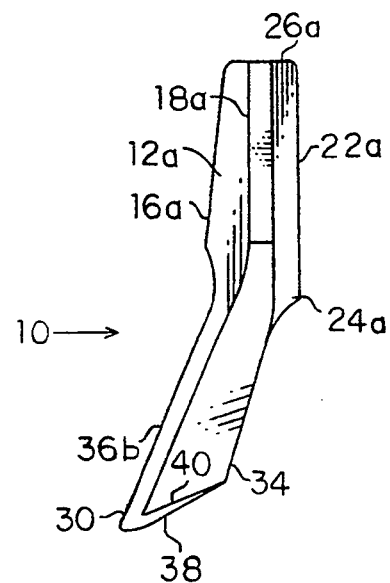
FIG. 2 is a side elevational view through section 2—2 of FIG. 1 of the bite block of the present invention.

FIGS. 1-5 illustrate various views of a bite block (10). More specifically, bite block (10) is seen to be comprised of a U-shaped body portion having a left wedge (12a) and a right wedge (12b), the wedges being substantially identical and integral with the U-shaped body. That is, wedges (12a) and (12b) are located at the distal end or terminus of leg portions (36a) and (36b), respectively, of U-shaped rib (14).

Turning now to the details of wedges (12a) and (12b), it can be appreciated (specifically in FIG. 2) that they form a distinct wedge-shaped body such that leading portion (24a) is thicker in cross-section than trailing portion (26a). Likewise, left wedge (12b) has a thicker cross-sectional leading portion than trailing portion. Thus, the term "wedge-shaped body" will be taken to mean thicker at the front, near, or proximal portion than at the rear, removed, or distal portion. The terms "front," "near" or "proximal" and "rear," "removed," or "distal" being determined with respect to the position of rib (14), the "front" being towards or closer to the rib and the "rear" being away or further from the rib.

Figure 13:
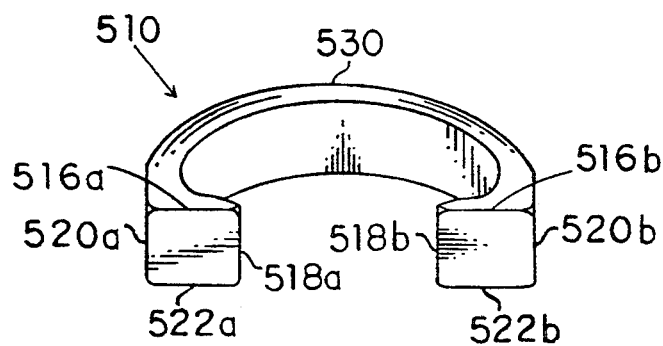
FIG. 13 is a rear elevation view of an alternate preferred embodiment of the applicant's present invention without inward or outward taper.

Wedges (12a) and (12b) have top surfaces (16a) and (16b) respectively, these surfaces being generally planar. Wedges (12a) and (12b) are further defined by inner side walls (18a) and (18b) respectively, and outer side walls (20a) and (20b) respectively, and bottom surfaces (22a) and (22b). It is to be appreciated from FIG. 4 that, besides having a distinctive wedge shape, wedges (12a) and (12b) may be tapered inwardly toward the inside of the mouth when the block (10) is inserted. That is, top surfaces (16a) and (16b) lie in non-parallel relation with corresponding bottom surfaces (22a) and (22b). Thus, inner side walls (18a) and (18b) are not as high or tall as outer side walls (20a) and (20b) respectively. This taper provides a beneficial improvement to the wedge, in that, when in use, as a patient bites down, the block is less likely to slip when gripped by the molars between the patient's upper and lower jaw. Slipping of the block in some cases could occlude the oral passageway. The rear terminus of wedges (12a) and (12b) is defined by surfaces (28a) and (28b), respectively. FIG. 13 illustrates a wedge without inward or outward taper and is discussed further below.

Figure 3:
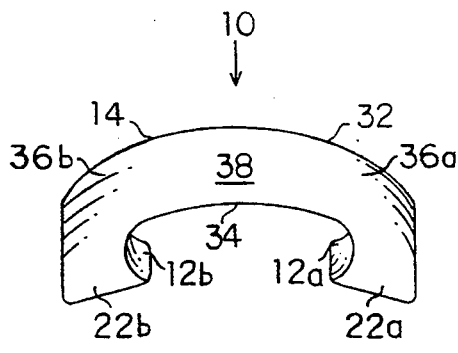
FIG. 3 is a front elevational view of the bite block of the present invention.
Figure 4:
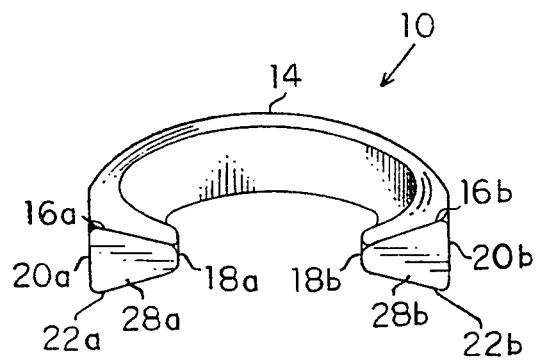
FIG. 4 is a rear elevational view of the bite block of the present invention with an inward taper.

Bite block (10) is an integral, one piece unit with wedges (12a) and (12b) being joined at a near or front end thereof by rib (14). As may be seen in all of the accompanying drawings, rib (14) is a solid member having no air passage orifice therein. Rib (14) is comprised of leg portions (36a) and (36b) which form forward extensions from the forward portions of wedges (12a) and (12b). The leg portions join ridge member (30) which is curved in two dimensions. That is, ridge member (30) has top surface (32) and bottom surface (34), as well as front surface (38) and rear surface (40). As seen in FIG. 1, ridge member (30) is curved to approximate the curve of the front teeth of the patient's upper jaw. As seen in FIG. 3, ridge member (30) also raises above the plane of bottom surfaces (22a) and (22b) of wedges (12a) and (12b). The curve as best appreciated in FIG. 1 approximates the curve of the dental ridge of the patient and allows for a flush fit as better viewed in FIGS. 6-9. The rise of rib (14) as illustrated in FIG. 3 is such that distance "d" in FIG. 8 provides clearance between the teeth of the patient's upper jaw and lower jaw for the insertion or accommodation of endotracheal tubes or the like beneath the rib (14). Specifically, at least a 9.0 mm. endotracheal tube or gastrointestinal endoscope may be inserted or accommodated. Angle $\theta$ defines the angle of the wedge taper.

Figure 7:
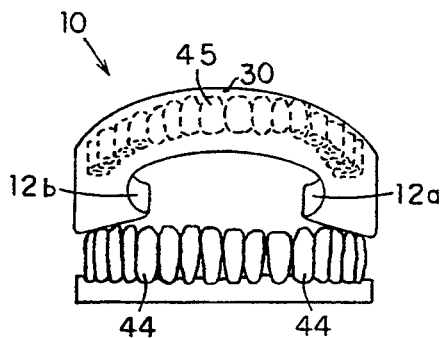
FIG. 7 is a front elevational view of the bite block of the present invention as inserted into a patient's mouth illustrating the position of the bite block with respect to the teeth of patient's upper and lower jaw.

FIGS. 6-8 also help illustrate the proper use of bite block (10). Bite block (10) is inserted into a patient's mouth such that top surfaces (16a) and (16b) and bottom surfaces (22a) and (22b) respectively are contacting molars (42). Due to the unique shape of bite block (10), the remaining teeth of the patient, whether incisors or front teeth, cannot contact any portion of bite block (10) in a compressional manner as do molar (42) on wedges (12a) and (12b), nor can the non-molars (44 and 45) contact one another. That is, the shape of wedges (12a) and (12b) provide clearance such that rib (14) carries no compressive forces between the jaw. It is understood that compressive forces mean those forces exerted during the clinching or clamping down of patient's jaw on bite block (10).

FIGS. 6-8 also illustrate how ridge member 30 with, inside, rear surface (40) contacting the upper front teeth (45) and/or gums of the patient prevents bite block (10) from sliding back into the mouth or the throat. Of course, bite block (10) could be inserted with ridge member (30) curving downward fitting snug against the patient's lower front tooth surfaces with the same effect. Thus, the bite block as set forth herein provides a unique shape combining wedges to hold the patient's mount open through contact with only the molars—teeth strong enough to bear these forces without damage. At the same time, a second tapering of the wedges provides for a secure, non-slip fit. The unique rib provides clearance with non-molars as well as clearance for the insertion of an endotracheal tube.

The bite block may be constructed of any non-toxic, resilient and durable material such as polyethylene, polypropylene and like polymeric resins.

Figure 9:
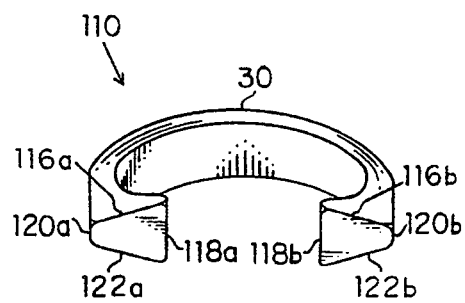
FIG. 9 is a rear elevational view of an alternate preferred embodiment of applicant's present invention with an outward taper.

FIG. 9 illustrates an alternate embodiment of bite block (110) wherein top and bottom surfaces (116a) and (122a) and (116b) and (122b) of wedges (112a) and (112b), respectively, are tapered outward such that inner side walls (118a) and (118b) are higher or taller than outer side walls (120a) and (120b). Such a taper would help prevent slipping of bite block (10) in patient's mouth.

Figure 10:
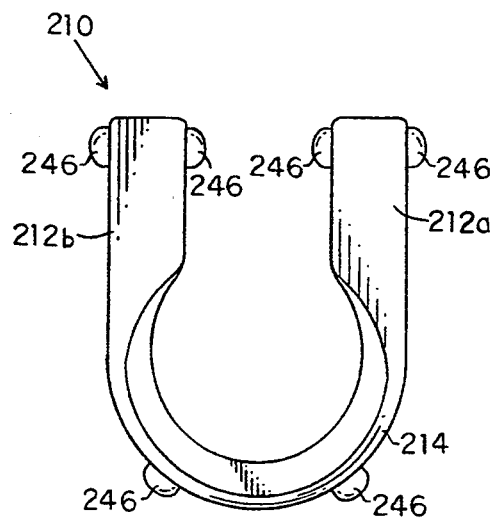
FIG. 10 is a top elevational view of an alternate preferred embodiment of applicant's present invention.

FIG. 10 illustrates yet another alternate embodiment of bite block (210), this embodiment is provided with vertical flange members (246) projecting upwardly and downwardly from wedges (212a) and (212b) and rib (214) to help position and maintain bite block (10) in patient's mouth by laying along the inner and outer side surfaces of the patient's teeth.

Figure 11:
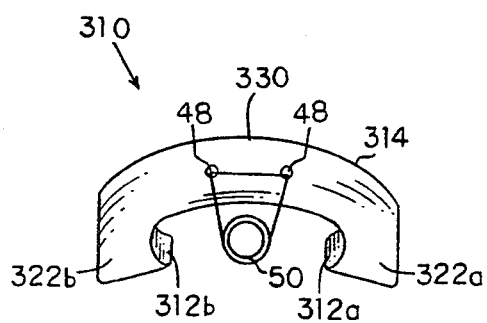
FIG. 11 is a front elevational view of an alternate preferred embodiment of applicant's bite block.

FIG. 11 illustrates yet another alternate embodiment of bite block (310) with walls defining holes (340) on ridge member (330). Holes (48) will help maintain the position of endotracheal tube (50) in relation to bite block (10) as, for example, through the use of plastic ties (51) or the like.

Figure 12A:
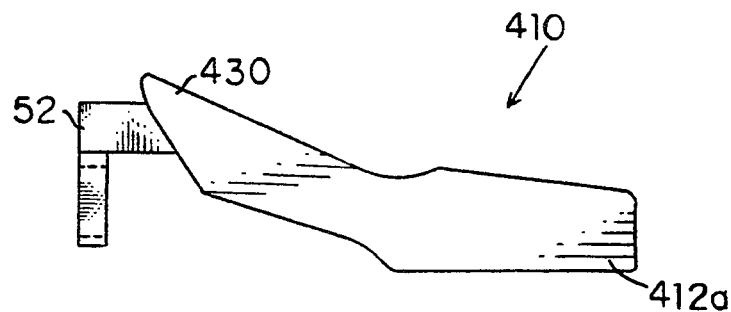
FIGS. 12A and 12B are a side elevational and front elevational view, respectively, of an alternate preferred embodiment of applicant's present invention.
Figure 12B:
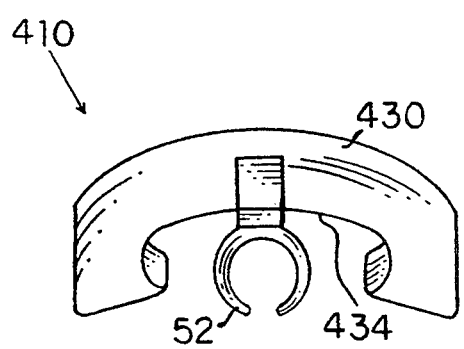

FIGS. 12A and 12B illustrate bite block (410) with an endotracheal tube attachment means (52) integral therewith. Specifically, FIGS. 12A and 12B illustrate endotracheal tube attachment means (52) as being a C-shaped piece of resilient material integral with ridge member (430) and centrally located thereon so as to project downward from bottom surface (434) of ridge member (430) to accept an endotracheal tube and position the same with respect to bite block (410).

FIG. 13 illustrates an alternate embodiment of the bite block (510) wherein top and bottom surfaces (516a) and (522a) and (516b) and (522b) of wedges (512a) and (512b), respectively, are not tapered inwardly or outwardly. Inner side walls (518a) and (518b) are the same height as outer side walls (520a) and (520b). While the embodiment of FIG. 13 does not provide the non-slippage feature discussed in the embodiments of FIGS. 4 and 9, the FIG. 13 embodiment is fully functional.

In addition, it may be understood that the wedges of the present invention may be shortened in length from front end to rear end so that the compression bearing portion is only over two sets of molars, rather than three. Of course, the bite block of the present invention may be dimensioned to various sizes having various lengths and widths so as to provide for the typical variety found in both children and adults.

Terms such as "left" "right" "up" "down" "bottom" "top" "front" "back" "in" "out" and the like are applicable to the embodiment shown and described in conjunction with the drawings. These terms are merely for the purposes of description and do not necessarily apply to the position or manner in which the invention may be constructed or used.

Although the invention has been described with reference to a specific embodiment, this description is not meant to be construed in a limiting sense. On the contrary, various modifications of the disclosed embodiments will become apparent to those skilled in the art upon reference to the description of the invention. It is therefore contemplated that the appended claims will cover such modifications, alternatives, and equivalents that fall within the true spirit and scope of the invention.

I claim:

1. A bite block for use with an endotracheally intubated patient, the bite block comprising:

a first wedge-shaped body for contacting only the patient's molars on one side of the patient's jaws and a second wedge-shaped body for contacting only the molars on the other side of the patient's jaws, said two bodies being substantially similar in shape, each body having a proximal end and a distal end, a generally planer top surface for contacting only upper molars and a generally planer bottom surface for contacting only lower molars, and generally planer walls defining an inner surface and an outer surface, said wedge-shaped bodies being thicker at said proximal end thereof than at said distal end thereof; and a solid rib, said rib being generally U-shaped and having no air passage orifice therein, said U-shaped rib having a first leg and a second leg, said first leg connected to said first wedge-shaped body at said proximal end thereof and said second leg connected to said second wedge-shaped body at the proximal end thereof, the legs of said rib connected by a curved ridge such that said bite block is bilaterally symmetrical about an axis centrally located on said ridge, said curved ridge having walls defining an upper edge and a lower edge said rib having a rise sufficient to accommodate an endotracheal tube beneath said rib;

wherein said bite block is insertable into the mouth of the patient and dimensioned to be held in place by compressional contact of only the patient's molars on said first and said second wedge-shaped bodies such that said rib is not subject to compressional contact.

2. The bite block as described in claim 1 wherein a lower edge of said ridge of said rib extends, at least in part, above a plane of a lower surface of either of said wedge-shaped bodies and an upper edge of said ridge of said rib extends, at least in part, above a plane of an upper surface of either of said wedge-shaped bodies.

3. The bite block as described in claim 2 wherein said top surfaces of said wedge-shaped bodies and said bottom surface of said wedge-shaped bodies taper inward such that said bodies are thinner along said inner surface than said outer surfaces.

4. The device as described in claim 2 wherein said top surfaces of said bodies and said bottom surface of said bodies taper outward such that said bodies are wider along said inner surface than said outer surfaces.

5. The bite block as described in claim 2 further including means for aligning and positioning said bite block in the patient's mouth.

6. The bite block as described in claim 2 further comprising means for securing an endotracheal tube thereto.

7. The bite block as described in claim 6 wherein said securing means comprises walls defining a hole in said ridge of said rib and a tie means for engagement with an endotracheal tube and said hole.

8. The bite block as described in claim 6 further comprising C-shaped brackets comprised of resilient lips and dimensioned for receipt of an endotracheal tube in a snug compression fit manner.

9. The bite block as described in claim 1 wherein said bite block is insertable into the mouth of the patient after an endotracheal intubation of the patient.

* * * * *